US011559411B2

(12) United States Patent
Kaltenborn et al.

(10) Patent No.: US 11,559,411 B2
(45) Date of Patent: Jan. 24, 2023

(54) PROSTHESIS AND PROSTHETIC FOOT ADAPTER (71) Applicant: Ottobock SE & Co. KGaA, Duderstadt (DE)

(72) Inventors: Sven Kaltenborn, Duderstadt (DE); Miclas Schwartz, Göttingen (DE); Ralf Allermann, Göttingen (DE); Sandra Vossler, Göttingen (DE); Sven Kubitz, Göttingen (DE)

(73) Assignee: Ottobock SE & CO. KGAA, Duderstadt (DE)

( * ) Notice: Subject to any disclaimer, the term of this patent is extended or adjusted under 35 U.S.C. 154(b) by 0 days.

(21) Appl. No.: 16/624,666

(22) PCT Filed: Jun. 19, 2018

(86) PCT No.: PCT/EP2018/066271
§ 371 (c)(1),
(2) Date: Dec. 19, 2019

(87) PCT Pub. No.: WO2019/007678
PCT Pub. Date: Jan. 10, 2019

(65) Prior Publication Data
US 2020/0179139 A1 Jun. 11, 2020

(30) Foreign Application Priority Data
Jul. 4, 2017 (DE) .................. 10 2017 114 892.2

(51) Int. Cl.
A61F 2/66 (2006.01)
A61F 2/50 (2006.01)

(52) U.S. Cl.
CPC ........ *A61F 2/66* (2013.01); *A61F 2002/5003* (2013.01); *A61F 2002/5007* (2013.01);
(Continued)

(58) Field of Classification Search
CPC .. A61F 2/60; A61F 2/66; A61F 2/6607; A61F 2/6614; A61F 2002/5039
See application file for complete search history.

(56) References Cited

U.S. PATENT DOCUMENTS 6,290,730 B1 * 9/2001 Pitkin ...................... A61F 2/66
623/49
6,764,521 B2 7/2004 Molino et al.
(Continued)

FOREIGN PATENT DOCUMENTS

CN 1819911 A 8/2006
DE 60005503 T2 6/2004
(Continued)

*Primary Examiner* — Bruce E Snow
(74) *Attorney, Agent, or Firm* — Holland & Hart LLP (57) ABSTRACT A prosthesis having a prosthetic foot with a forefoot area and a heel area, a prosthetic lower leg, and a prosthetic foot adapter for arranging the prosthetic foot on the prosthetic lower leg. The prosthetic foot adapter includes an upper part for fixing it to the prosthetic lower leg such that it is torque-proof in relation to a sagittal plane, a lower part for fixing it to the prosthetic foot such that it is torque-proof in relation to a sagittal plane, and a resistance element. The upper part can be swivelled on the lower part about a swivel axis against a restoring force exerted by the restoring element, the swivel axis extending from the heel area to the forefoot area.

15 Claims, 6 Drawing Sheets (52) U.S. Cl.
CPC ............... *A61F 2002/5039* (2013.01); *A61F 2002/5072* (2013.01); *A61F 2002/6614* (2013.01)

(56) References Cited

U.S. PATENT DOCUMENTS

| | | |
|---|---|---|
| 7,044,984 B2 | 5/2006 | Kuiken |
| 2014/0200680 A1 | 7/2014 | Holgate et al. |
| 2016/0058581 A1 | 3/2016 | Maitland |
| 2016/0331559 A1 | 11/2016 | Maitland et al. |
| 2016/0367384 A1* | 12/2016 | Sigmon ................ A61F 2/76 |
| 2018/0338844 A1* | 11/2018 | Hippensteal ........... A61F 2/601 |
| 2020/0179139 A1* | 6/2020 | Kaltenborn ........... A61F 2/6607 |

FOREIGN PATENT DOCUMENTS

| | | |
|---|---|---|
| DE | 102004037877 A1 | 2/2006 |
| DE | 102014116240 B4 | 6/2016 |
| GB | 2177925 A | 2/1987 |

\* cited by examiner

PROSTHESIS AND PROSTHETIC FOOT ADAPTER

CROSS REFERENCE TO RELATED APPLICATIONS

This application is a U.S. National Entry and claims priority to PCT International Patent Application No. PCT/EP2018/066271, filed 19 Jun. 2018, and entitled "PROSTHESIS AND PROSTHETIC FOOT ADAPTER," which claims priority to Germany Patent Application No. 10 2017 114 892.2 filed 4 Jul. 2017, the entire disclosures of which are incorporated herein by this reference.

TECHNICAL FIELD

The invention relates to a prosthesis with a prosthetic foot, with a forefoot area and a heel area, a prosthetic lower leg and a prosthetic foot adapter for arranging the prosthetic foot on the prosthetic lower leg.

BACKGROUND

This type of prosthesis has been known within the scope of the prior art for many years. The aim of such prostheses is to give people with a leg that had to be amputated above or below the knee the opportunity to walk using the prosthesis, and to provide the respective user of the prosthesis with as natural a gait cycle as possible with the highest possible degree of stability and safety. A range of approaches to constructing such a prosthesis are known from the prior art. For example, U.S. Pat. No. 6,764,521 B2 presents a relevant prosthesis. The prosthetic foot is arranged on a prosthetic lower leg via a prosthetic foot adapter. Here, the prosthetic foot adapter is designed in such a way that it can be guaranteed that the prosthetic foot can swivel multi-axially relative to the prosthetic lower leg. This should enable the imitation of the natural movement options of a healthy foot. In this case, a swivel axis that extends from medial to lateral imitates the upper ankle joint or the ankle joint. It enables a movement of the foot in the dorsal flexion and plantar flexion direction. In addition, a second rotational axis or swivel axis is provided, which extends vertically to this first axis and enables a swivelling of the foot in the medial and lateral direction. This should ensure a sufficient degree of stability and full contact with the ground, when treading, for example, on slanted surfaces, such as standing on a slope.

DE 10 2004 037 877 A1 takes a similar approach. It also describes a prosthetic device with a prosthetic foot that is arranged on a prosthetic lower leg, wherein a universal joint is arranged between the, two structural components. Said universal joint has two rotational axes, which are perpendicular to one another, that correspond to the previously described axes and enable a movement of the foot about two swivel axis. which are arranged orthogonally to one another.

However, it is disadvantageous that the installation space required for such prostheses and especially for prosthetic foot adapters for such prostheses is relatively large, so that—where applicable—such a prosthetic foot adapter cannot be fully accommodated in a foot shell in particular. Here, a prosthetic shell is a plastic casing, for example, which can be arranged around the actual prosthetic foot to lend it as natural an appearance as possible.

U.S. Pat. No. 7,044,984 B2 therefore presents a prosthetic foot that does not have a separate prosthetic foot adapter. In lieu of this, the prosthetic foot comprises an accommodation into which a part of the prosthetic lower leg can be inserted in such a way that both structural components are connected to one another such that they can be only swivelled about one swivel axis. This axis enables a swivelling of the prosthetic foot relative to the prosthetic lower leg in the medial and lateral direction and consequently extends from the heel area of the prosthetic foot to the forefoot area. To be able to imitate a movement of the ankle joint, the prosthetic lower leg is made of a resilient material, such as a carbon fiber composite material. Therefore, no separate joint is provided; rather, the capacity for movement is achieved by way of the elasticity and spring effect of the prosthetic lower leg.

The disadvantage of all the embodiments described above is that, in certain situations of movement, the wearer of the respective prosthesis may experience a feeling of unsteadiness and instability. The invention thus aims to remedy these dis-co advantages or at least to reduce them.

SUMMARY

The invention solves the problem by way of a prosthesis with a prosthetic foot, with a forefoot area and a heel area, a prosthetic lower leg and a prosthetic foot adapter for arranging the prosthetic foot on the prosthetic lower leg, wherein the prosthetic foot adapter comprises an upper part for fixing it—in relation to a sagittal plane—to the prosthetic lower leg such that it is torque-proof; a lower part for fixing it—in relation to a sagittal plane—to the prosthetic foot such that it is torque-proof; and a resistance element, wherein the upper part can be swivelled on the lower part, against a resistance applied by the resistance element, about a swivel axis, said swivel axis extending from the heel area to the forefoot area.

The invention is based on the surprising knowledge that, to ensure a gait pattern that is sufficiently natural in many cases as well as an increased degree of stability and security for the wearer of the prosthesis, it is sufficient for the upper part to be arranged on the lower such that it can be only swivelled about one swivel axis and for no other twisting or movement of the prosthetic lower leg relative to the prosthetic foot to be provided for. It is also not necessary for the prosthetic lower leg to be designed to be elastic or resilient. A swivelling or movement of the prosthetic foot relative to the prosthetic lower leg in the form of a dorsal flexion or plantar flexion is not necessary and preferably not possible with a prosthesis according to the present invention. In particular, this means that the prosthetic lower leg and the position of the swivel axis relative to a longitudinal axis of the prosthetic lower leg do not deform or change, or at least not to a considerable degree, upon being subjected to the loads that are applied to the prosthesis by the wearer during walking or standing whilst using the prosthesis. It is particularly preferable if an angle be-tween the swivel axis and the longitudinal direction of the prosthetic lower leg re-mains almost or completely constant in all load situations that occur during operation and use of the prosthesis.

Here, the sagittal plane is a plane that is formed by a longitudinal direction of the prosthetic lower leg and a longitudinal direction of a prosthetic foot, which is to be arranged on the prosthetic foot adapter. It corresponds to the sagittal plane on the human body, known from the field of orthopedics, in which the given longitudinal directions lie. In a healthy human ankle, the upper ankle joint allows for such a rotation or swivelling within the sagittal plane: this is not possible according to the invention. A torsion or rotation about the longitudinal direction of the prosthetic lower leg and/or a displacement—for instance as a shock absorption—along the longitudinal direction of the prosthetic lower leg are preferably possible with the type of prostheses described here.

The resistance element is preferably a restoring element that exerts a restoring force, a damper, a spring element, such as a helical spring or a leaf spring, or a friction element, wherein resistance against the swivelling is generated by way of friction. Specifically, a restoring element or spring element has been proven to be practical, since a force is generated by these elements upon swivelling, said force bringing the upper part and the lower part back towards each other into the original position or at least rendering more simple and supporting such a swivelling in the opposite direction to the original swivelling.

In a preferred embodiment, the prosthetic lower leg has a longitudinal axis, and the swivel axis and the longitudinal axis form an angle that is not 90°. It has proven to be especially beneficial if the swivel axis is tilted towards the forefoot area. This means that a distance of the swivel axis relative to a ground on which the prosthetic foots lies is smaller in the forefoot area than in the heel area.

This results in several advantages. Given that the swivel axis, about which the upper part can be swivelled relative to the lower part and therefore also the prosthetic lower leg fixed to the upper part can be swivelled relative to the prosthetic foot fixed to the lower part, does not extend in the contact surface between the prosthetic foot and the ground, a swivelling of the prosthetic foot relative to the prosthetic lower leg about this swivel axis not only results in a change in the tilt of the foot, but also in a change in the position of the tread surface of the prosthetic foot. Upon a swivelling about the swivel axis, the tread surface moves along a circular path about the swivel axis. The greater the distance between the swivel axis and the tread surface of the prosthetic foot, the larger the radius of this circular path, such that a swivelling about a certain angle has a considerably greater influence on the displacement of the tread surface. It is therefore beneficial to place the swivel axis as close as possible to the contact surface of the foot, so as to ensure that the wearer of the prosthesis does not feel that their standing position is un-steady or that they are lacking in stability. In the present case, this is preferably achieved by the swivel axis being tilted towards the forefoot area in such a way that, in this area, the distance between the swivel axis and the tread surface is especially small, and therefore this area is perceived as being particularly stable. At the same time; the tilted arrangement of the swivel axis in the heel area of the prosthetic foot ensures that there is sufficient installation space to integrate heel functions, if desired. This may be achieved, for instance, by way of spring elements, such as leaf springs, or heel padding, for example made of a foam or elastomer, as is known from the prior art; these serve, for example, to absorb any forces which may occur when the heel strikes the ground.

Furthermore, the tilted swivel axis enables the installation space available within a foot shell to be utilized more effectively, since said installation space is also tilted towards the forefoot.

A further advantage is a combined movement that occurs between the prosthetic lower leg and the prosthetic foot, which occurs as a result of the tilted swivel axis. For instance, if the wearer of the prosthesis strikes a tilted surface with the prosthetic foot, such that the outer edge of the foot has lowered once the foot has struck the surface and is stable, the tilted swivel axis of the prosthetic lower leg rotates inwards. During the opposing movement, in which the outer edge of the prosthetic foot rises in relation to the inner edge, the prosthetic lower leg rotates outwards. The force of this simultaneous rotation depends on the angle between the swivel axis and the longitudinal axis of the prosthetic lower leg. This angle preferably lies between 95° and 120°, especially preferably between 100° and 110°; it is particularly preferable if said angle is 105°.

This combined movement has several effects, each of which is beneficial. When walking on a plane, the beginning of the stance phase of a gait cycle is marked by an inward rotation of the prosthetic lower leg relative to the foot; during the roll-out process, said prosthetic lower leg returns to the neutral position. If the prosthetic lower leg rotates inwards at the beginning of the stance phase, the tilted swivel axis effects an inversion of the prosthetic foot, such that the outer edge of the prosthetic foot lowers. The force transmission point of the foot is thus displaced towards the outer edge of the foot, which corresponds to the natural progression in a healthy foot. During the roll-out of the foot, the prosthetic lower leg is rotated back into the neutral position, such that the inversion is also compensated for and the force transmission point moves in the medial/lateral direction back to the central part of the foot if the roll-over of the foot causes a displacement of said force transmission point into the forefoot region.

The second effect of the combined movement relates to walking or standing on a slope. The slope causes the foot to be pressed into the inversion, in which the outer edge of the foot is lowered. The respective other foot is pressed into the inversion, in which the outer edge is raised relative to the inner edge of the prosthetic foot. This results in a corresponding rotation of the prosthetic lower leg, which always occurs in the uphill direction when on a slope; this creates a sense of greater security.

As a result of this especially preferable configuration of a swivel axis that is tilted towards the forefoot area, the sense of security on the slope is increased and the gait pattern reflects that of a natural foot.

Preferably, the restoring element features at least one torsion bar. For instance, this may be a bar made of a material that generates a restoring force upon being twisted, i.e. under a torsion. The bar may be made, for example, of titanium or another metal, or at least contain such a metal. If a sufficient degree of stiffness and resistance is achieved, an elastic and, where appropriate, non-metallic material may be used. The bar is arranged in such a way that a swivelling of the upper part relative to the lower part at least also leads to a twisting of the torsion bar, which generates a restoring force. Of course, other restoring elements, such as compression springs, tension springs, elastomer components or other dampers are also possible. Magnets with the same polarity and that consequently repel each other may also be used as restoring elements. Of course, adjustable electromagnets or combinations of several of the solutions named above may also be used
as a restoring element. The advantage of compression and tension springs, and of course of combined tension-compression springs, elastomer components and metal bars, such as the torsion bar, is that the restoring force increases as the swivel angle increases. Consequently, the stronger the upper part is swivelled relative to the lower part, the greater the restoring force. This can also be achieved with magnetic restoring elements, which comprise, for instance, magnets that are arranged to repel each other. They may be arranged to be cascading, such that, upon a stronger swivelling of the upper part relative to the lower part, more magnets move into the respective effective range of an opposing magnet with the same polarity. This increases the restoring force. However, the restoring force is already increased, for instance, by way of a reduction in a distance between the homopolar magnets if the swivelling of the upper part relative to the lower part in-creases.

A torsion bar requires very little installation space and is therefore especially practical for prostheses which comprise a small prosthetic foot, such as child prostheses. However, it may of course also be used effectively with other prostheses. In this case, it is preferably arranged such that the swivel axis extends in its interior. This does not mean that the swivel axis is a separate structural component that is arranged inside the torsion bar. In this case, the swivel axis is merely a theoretical construction. A swivelling of the upper part relative to the lower part only results in a twisting of the torsion bar. Alternatively or additionally, at least one torsion bar may be arranged outside of the swivel axis, such that, in addition to the twisting or torsion, a deflection also occurs, which gives rise to additional restoring forces.

The torsion bar is preferably arranged in a hollow shaft, which is preferably connected to the upper part or the lower part such that it is torque-proof. Preferably, the torsion bar is also at least positively connected to the torsion bar. It is especially preferable if it is only positively connected. This may be achieved, for instance, by way of a polygon, particularly a triangle, and a screw, particularly a set screw. The arrangement in a hollow shaft protects the mechanism from environmental influences and reduces a potential risk of jamming.

The at least one torsion bar preferably has a circular cross-section. This enables an even distribution of the shear stress on the lateral surface of the torsion bar.

In a preferred embodiment, a swivelling of the upper part relative to the lower part is restricted in at least one direction, preferably in both swivel directions, by at least one end stop, preferably two end stops. Said end stops may be reached, for example, when the upper part is swivelled so far relative to the lower part that it strikes the lower part. Of course, separate end stops may be provided which are preferably adjustable, so that a maximum swivel angle and/or the size of the swivel range can be adjusted. In addition, the prosthetic foot adapter preferably has at least one end stop element, preferably at least two end stop elements, by means of which a striking on one or both end stops is damped. These may be designed as hard end stop elements or may feature a certain degree of damping if, for ex-ample, they are designed in the form of a spring element or an elastic element. The end stop elements and the restoring element can be fully enclosed in a housing or by the upper part or the lower part, such that, for instance, any contamination is largely ruled out.

In a preferred embodiment, the resistance element and specifically the resistance applied by said element and/or the at least one end stop element can be replaced and/or adjusted, The prosthesis preferably has a locking device which can be brought into a locking position, in which a swivelling of the upper part relative to the lower part is not possible. The locking device may feature, for example, a cotter pin, which can be displaced or rotated and which, in at least one position or orientation, prevents a swivelling relative to the rest of the prosthesis. Of course, the locking device may be designed to be hydraulic, pneumatic or electronic.

The invention also solves the task at hand by way of a prosthetic foot adapter for a prosthesis as described here.

In the following, an example of an embodiment of the present invention will be explained in more detail by way of the attached figures: They show:

Figure 1:
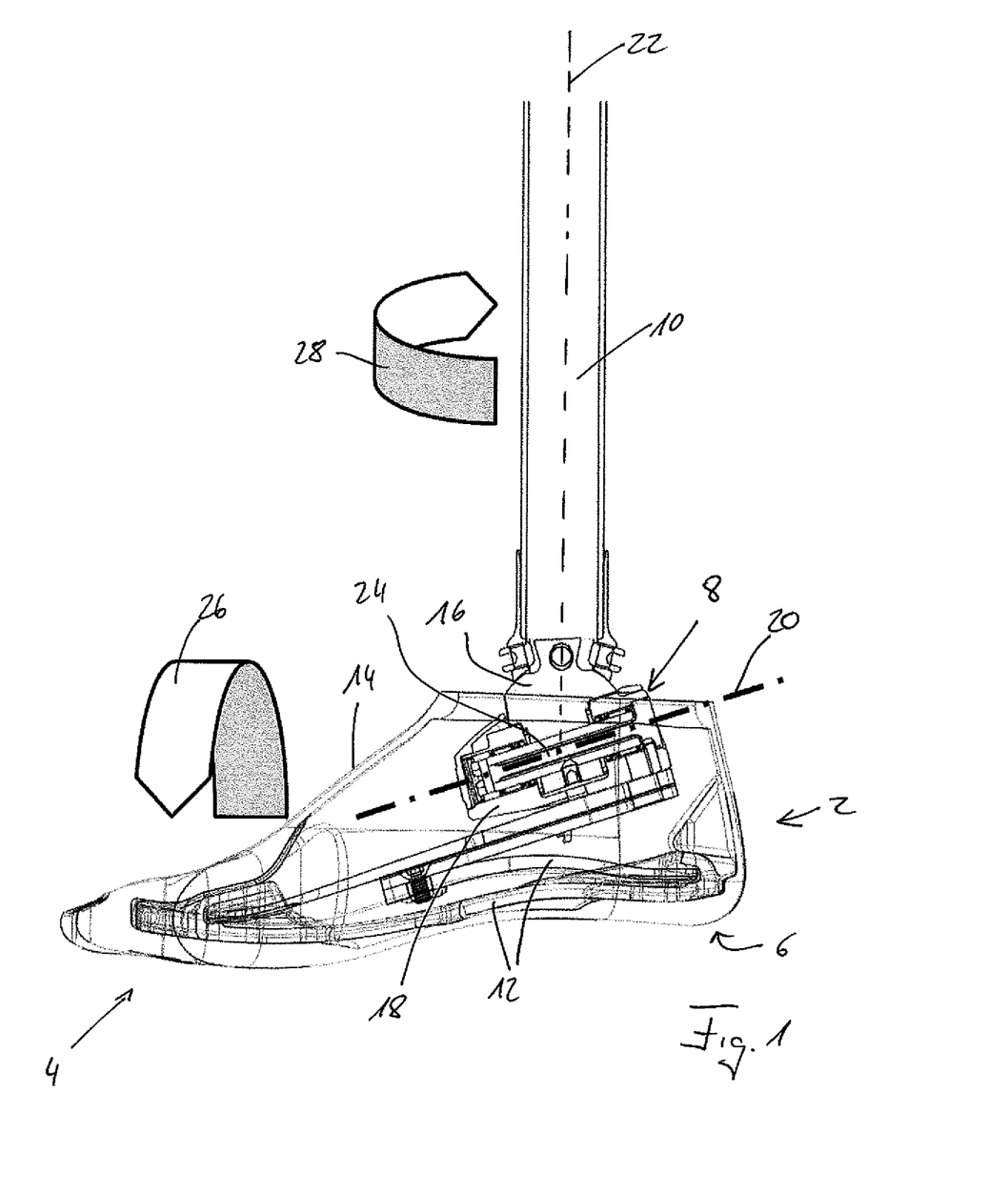
FIG. 1—the schematic sectional view through a prosthesis according to a first example of an embodiment of the present invention, FIG. 2—a schematic three-dimensional view of the prosthesis, FIG. 3—the schematic top view of a prosthetic foot with a prosthetic foot adapter according to an example of an embodiment of the present invention, FIG. 4—the schematic sectional view through a prosthetic foot adapter, FIG. 5—a sectional view through a prosthetic foot adapter along another plane, FIG. 6—the schematic sectional view through an artificial foot, FIG. 7—the schematic sectional view through a special configuration of a restoring element, and FIG. 8—the schematic view of a restoring force.

FIG. 1 depicts the schematic sectional view through a prosthesis according to a first example of an embodiment of the present invention. Said prosthesis comprises a prosthetic foot 2, which has a forefoot area 4 and a heel area 6. The prosthetic foot 2 is connected to a prosthetic lower leg 10 via a prosthetic foot adapter 8.

The prosthetic foot 2 features several leaf springs 12, which determine the resilient properties of the prosthetic foot 2. They are enclosed by a foot shell 14. Said foot shell, which should lend the prosthetic foot 2 as natural an appearance as possible, restricts the installation space available for the prosthetic foot adapter 8.

DETAILED DESCRIPTION

The prosthetic foot adapter 8 features an upper part 16, on which the prosthetic lower leg 10 is arranged such that it is torque-proof. It also has a lower part 18, which is connected to the prosthetic foot 2 such that it is torque-proof. The upper part 16 can be swivelled relative to the lower part 18 about a swivel axis 20, which—in FIG. 1—is tilted relative to a longitudinal axis 22 of the prosthetic lower leg 10 and does not form a right angle.

A restoring element 24 is situated inside of the prosthetic foot adapter 8, said restoring element applying a restoring force if the upper part 16 is swivelled relative to the lower part 18.

Since the swivel axis 20 is tilted, a swivelling of the prosthetic foot 2 in the direction of the first arrow 26 when the prosthesis is subjected to a load causes the prosthetic lower leg 10 to be rotated in the direction of the second arrow 28. This combined movement has already been described in detail.

Figure 2:
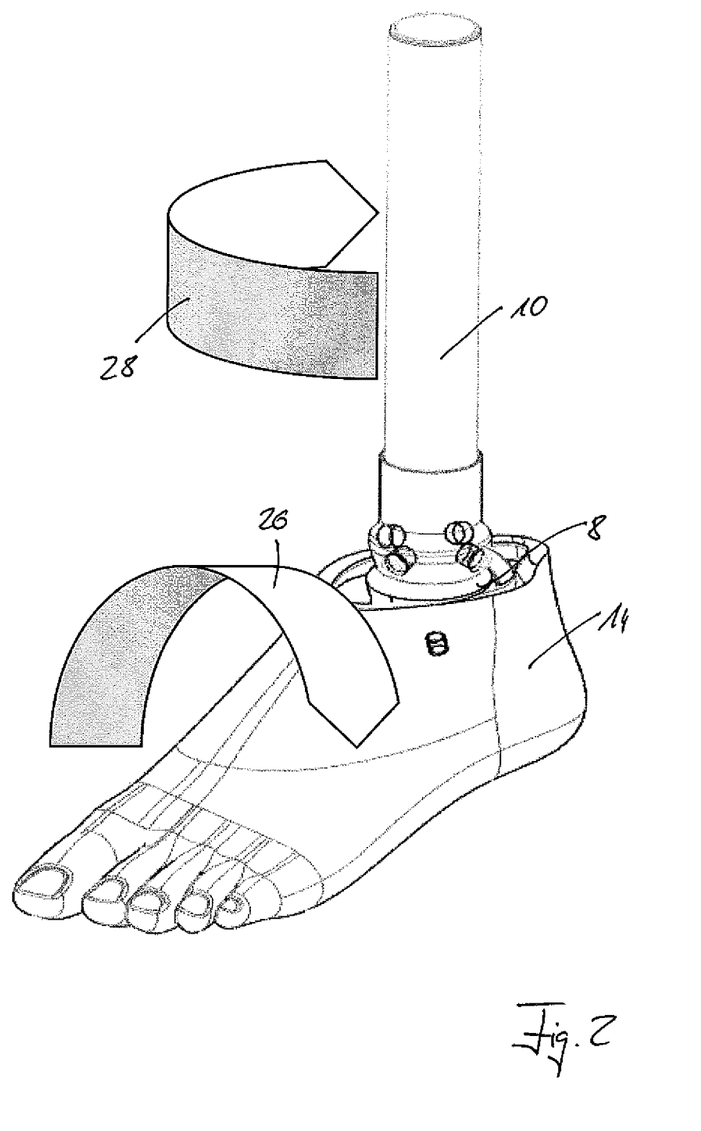

FIG. 2 shows the prosthesis in a schematic 3D view. Both the foot shell 14 and the prosthetic lower leg 10 can be clearly recognized, the latter being arranged on the prosthetic foot adapter 8. A rotation of the prosthetic foot 2 in the direction of the first arrow 26 causes the prosthetic lower leg 10 to be rotated in the direction of the second arrow 28 if, as is the case in the example of the embodiment shown, the swivel axis 20 is tilted relative to the contact surface of the prosthetic foot and therefore does not form a right angle with the longitudinal axis 22 of the prosthetic lower leg 10.

Figure 3:
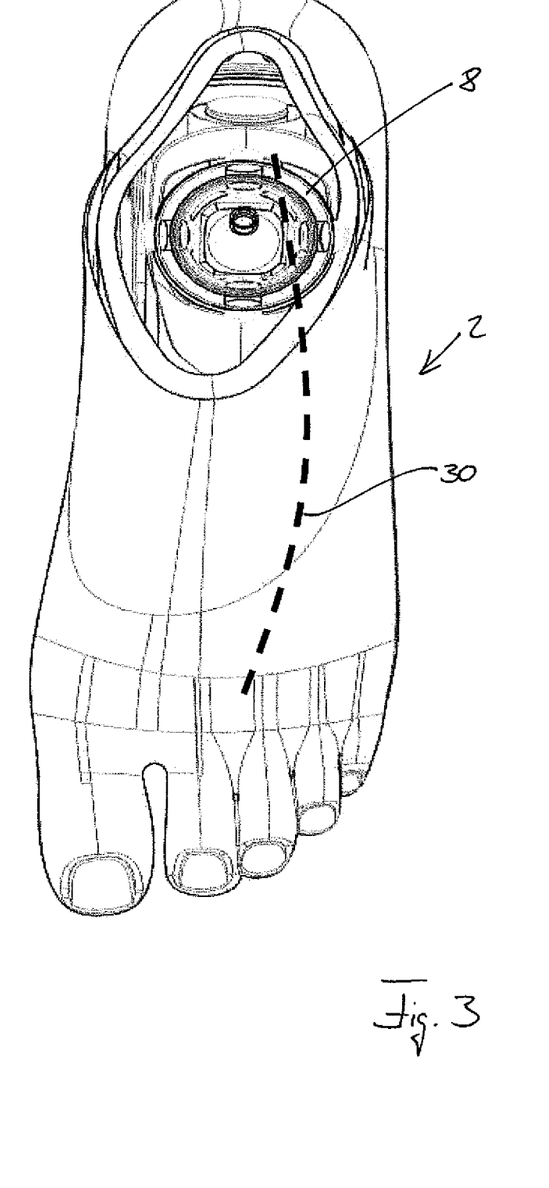

FIG. 3 depicts the prosthetic foot 2 with the prosthetic foot adapter 8 in a schematic top-view. The dashed line 30 schematically depicts the progression of the force transmission point over the course of a step. It is clear that the progression is considerably closer to the natural progression, during which the force transmission point is also displaced towards the lateral side of the foot, i.e. towards the outer edge, than the progression in conventional prosthetic feet.

Figure 4:
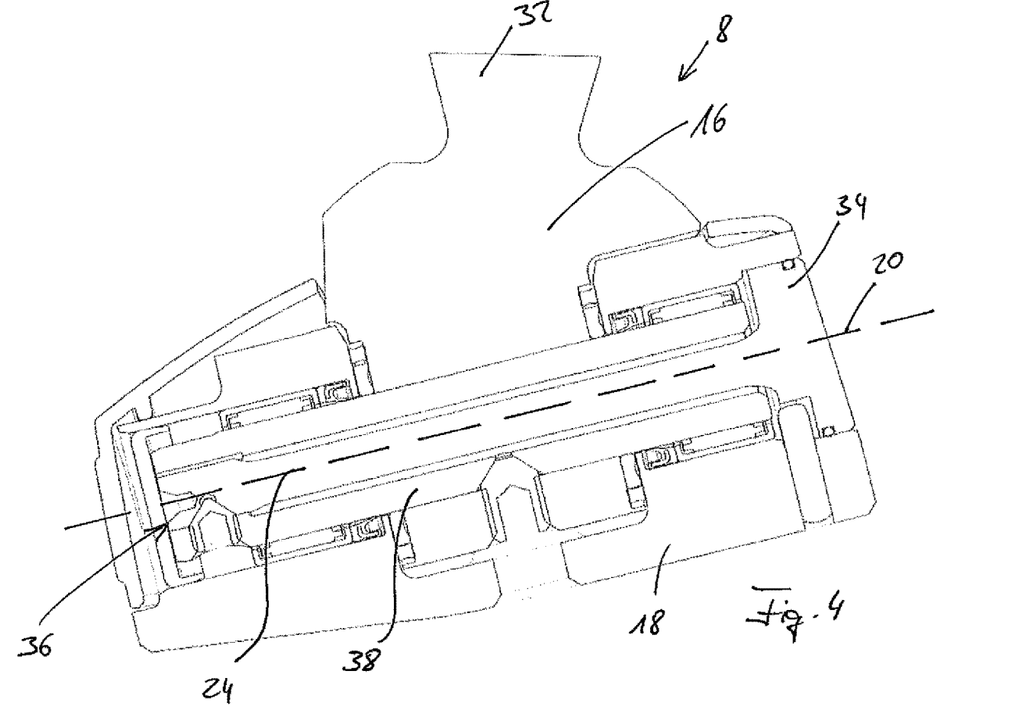

FIG. 4 shows an enlarged sectional view through the prosthetic foot adapter 8. The prosthetic lower leg 10 may be arranged on a fixing element 32. The fixing element 32 is part of the upper part 16, which is mounted such that it can be swivelled relative to the lower part 18 about the swivel axis 20. A restoring element 24 in the form of a torsion bar is situated inside. The heel end 34 of said torsion bar is connected to the lower part such that it is torque-proof; the forefoot end 36 is fixed to the upper part 16 such that it is torque-proof. If the upper part 16 and the lower part 18 are now swivelled relative to one another, it causes a torsion of the restoring element 24, which is mounted in a hollow shaft 38, and therefore the application of a resorting force.

Figure 5:
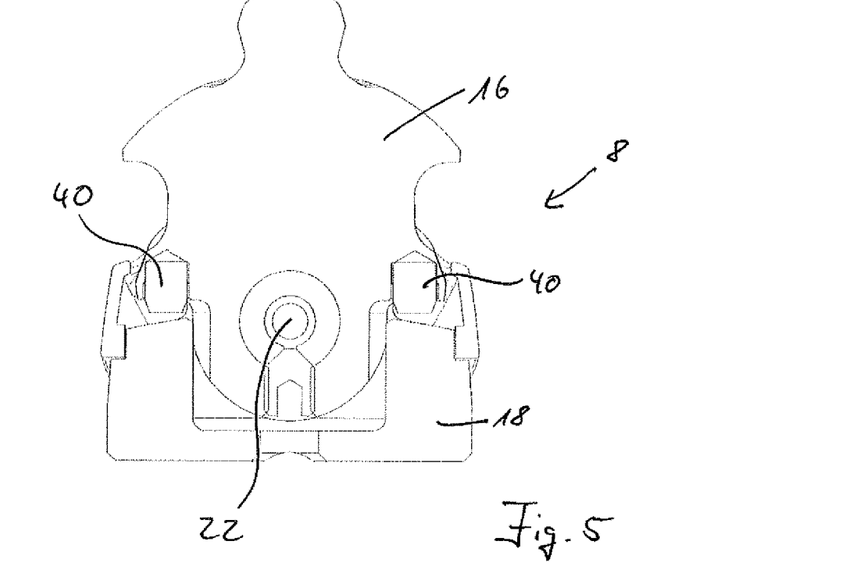

FIG. 5 shows a schematic sectional view in a plane that is perpendicular to the sectional plane in FIG. 4. The upper part 16 and the lower part 18 can be clearly recognized, as can the longitudinal axis 22 about which the upper part 16 can be swivelled relative to the lower part 18. Furthermore, the prosthetic foot adapter 8 shown in FIG. 5 has two end stop elements 40, by way of which a striking of the upper part 16 on the lower part 18 is damped, wherein said striking may occur if a maximum swivel angle is reached in both directions.

Figure 6:
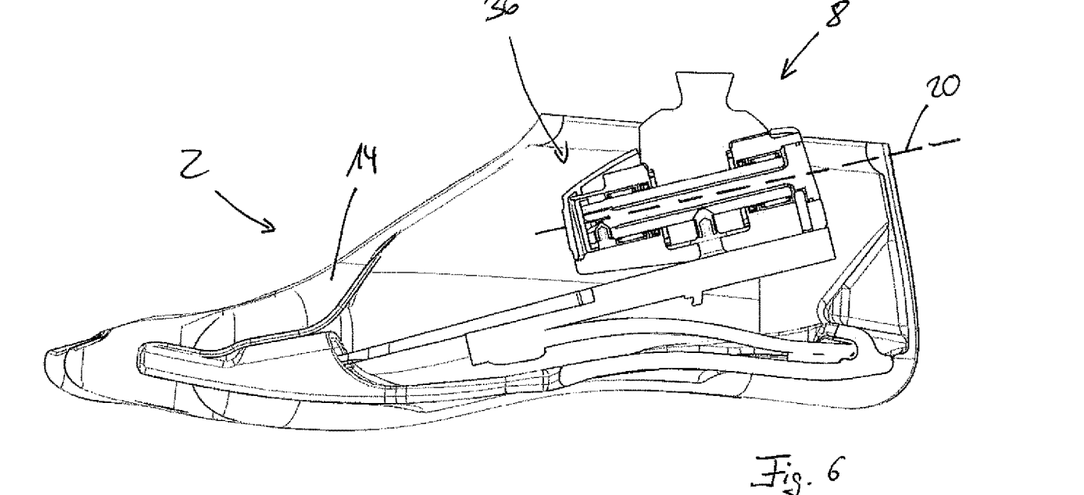

FIG. 6 depicts the prosthetic foot adapter from FIG. 4 in a prosthetic foot 2. Due to the tilting of the swivel axis 20, the prosthetic foot adapter 8 fits better—especially at its forefoot end 36—in an installation space created by the foot shell 14.

Figure 7:
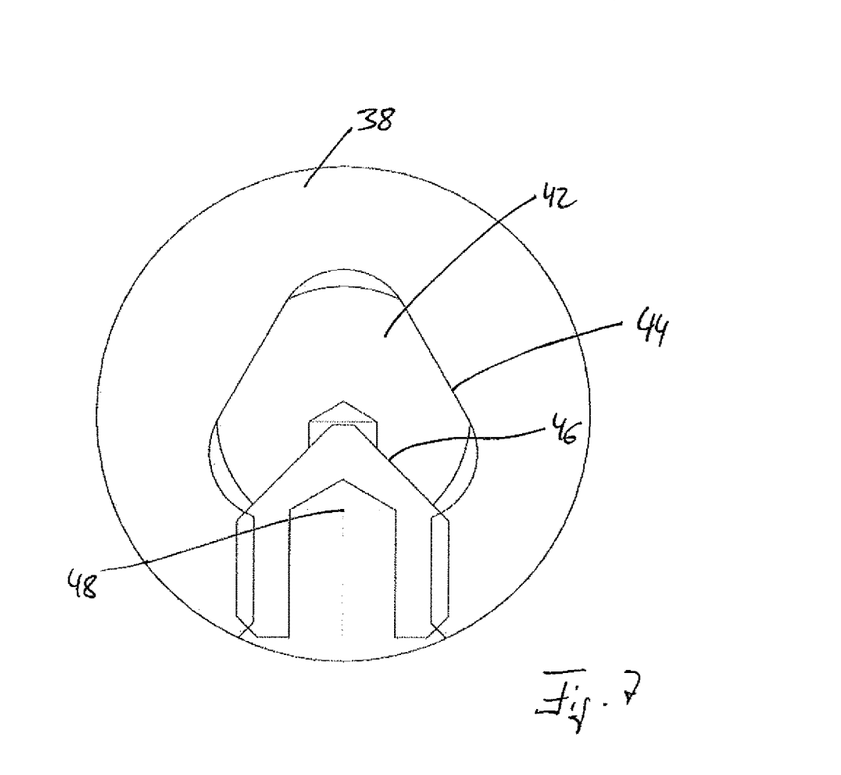

FIG. 7 shows a sectional view perpendicular to the direction of extension of the restoring element 24. The restoring element 24 is designed as a torsion bar 42 and arranged in a hollow shaft 38. Said shaft features an inner triangle 44 to which the outer shape of the torsion bar 42 adjusts by way of an outer triangle. The torsion bar 42 also features a conical bore 46, in which a set screw 48 or a threaded pin is arranged.

Figure 8:
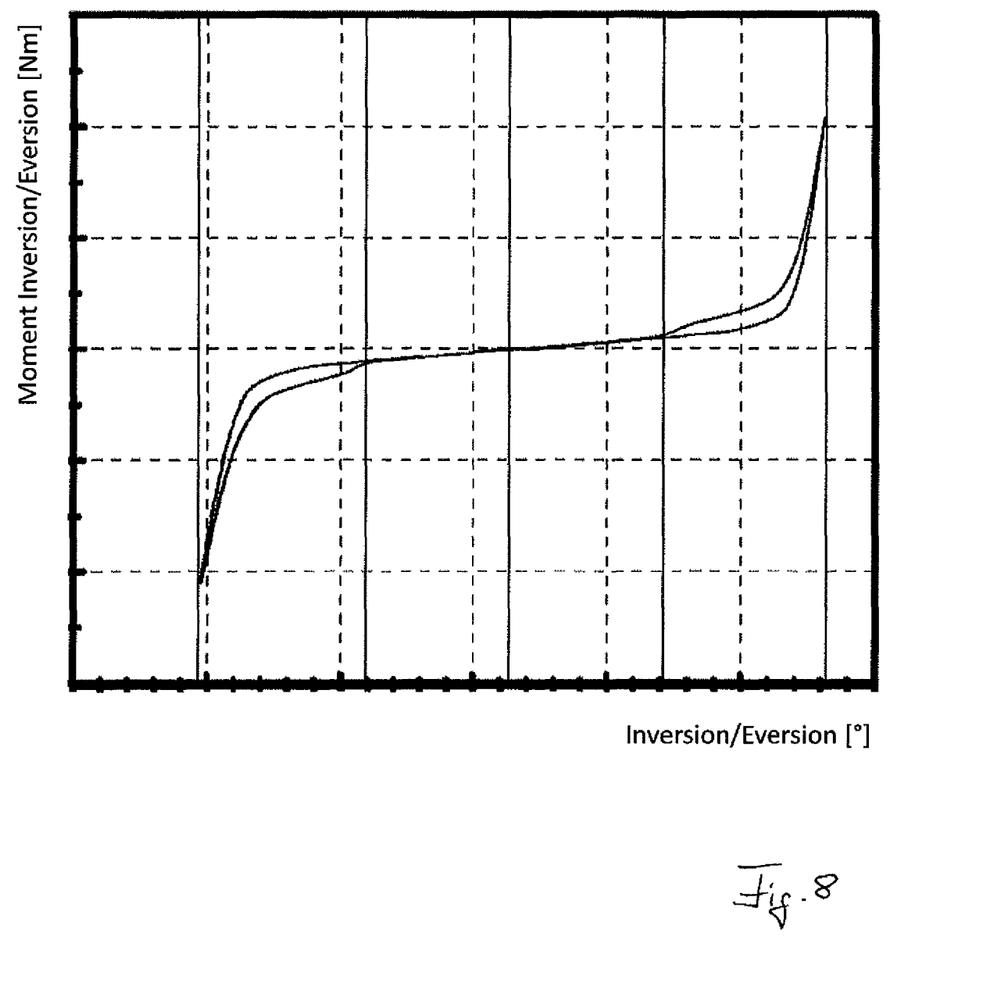

FIG. 8 shows the relationship between an inversion or eversion of the foot, i.e. a swivelling about the swivel axis 20, and a corresponding torque, wherein the former is plotted on the horizontal axis, i.e. the x axis in the diagram, and the latter on the vertical axis, i.e. the y axis. It is clear that particularly by activating and/or deactivating additional torsion elements or restoring elements 24, an almost arbitrary relationship can be established. In the example of an embodiment shown, the eversion and inversion resistance initially develop in a linear manner. After approximately half of the angle range, it progresses in such a way that ultimately a further inversion or further eversion beyond the critical angle is not possible or at least difficult.

We claim:

1. A prosthesis comprising:
   a prosthetic foot with a forefoot area and a heel area;
   a prosthetic lower leg; and
   a prosthetic foot adapter for arranging the prosthetic foot on the prosthetic lower leg, the prosthetic foot adapter comprising:
   an upper part for fixing the prosthetic foot adapter to the prosthetic lower leg such that a swiveling movement in the form of a dorsal flexion or a plantar flexion of the prosthetic foot adapter relative to the prosthetic lower leg is prevented;
   a lower part for fixing the prosthetic foot adapter to the prosthetic foot such that a swiveling movement in the form of a dorsal flexion or a plantar flexion of the prosthetic foot adapter relative to the prosthetic foot is prevented; and
   a resistance element comprising at least one torsion bar;
   wherein the upper part can be swiveled on the lower part about a swivel axis against a resistance exerted by the resistance element, the swivel axis extending from the heel area to the forefoot area of the prosthetic foot.

2. The prosthesis according to claim 1, wherein the swivel axis is tilted towards the forefoot area.

3. The prosthesis according to claim 1, wherein the at least one torsion bar is arranged inside a hollow shaft, which is preferably connected to the upper part or the lower part such that a swiveling movement in the form of a dorsal flexion or a plantar flexion of the hollow shaft relative to the upper part or the lower part is prevented.

4. The prosthesis according to claim 3, wherein the torsion bar is at least also positively connected to the hollow shaft.

5. The prosthesis according to claim 1, wherein the at least one torsion bar has a circular cross-section.

6. The prosthesis according to claim 1, wherein a swiveling of the upper part relative to the lower part in at least one direction is restricted by at least one end stop, and the prosthetic foot adapter comprises at least one end stop element by way of which a strike is damped.

7. The prosthesis according to claim 6, wherein at least one of the resistance element and the at least one end stop element can be at least one of replaced and adjusted.

8. The prosthesis according to claim 1, further comprising a locking device which can be brought into a locked position, in which a swiveling of the upper part relative to the lower part is prevented.

9. A prosthetic foot adapter for a prosthesis, comprising:
   an upper part to fix the prosthetic foot adapter to a prosthetic lower leg such that a swiveling movement in the form of a dorsal flexion or a plantar flexion of the prosthetic foot adapter relative to the prosthetic lower leg is prevented;
   a lower part to fix the prosthetic foot adapter to the prosthetic foot such that a swiveling movement in the form of a dorsal flexion or a plantar flexion of the prosthetic foot adapter relative to the prosthetic foot is prevented; and
   a resistance element comprising at least one torsion bar;
   wherein the upper part can be swiveled on the lower part about a swivel axis against a resistance exerted by the resistance element, the swivel axis extending from a heel area to a forefoot area of a prosthetic foot.

10. A prosthesis comprising:
    a prosthetic foot with a forefoot area and a heel area;
    a prosthetic lower leg;
    a prosthetic foot adapter to arrange the prosthetic foot on the prosthetic lower leg, the prosthetic foot adapter comprising:
    an upper part to fix the prosthetic foot adapter to the prosthetic lower leg such that a swiveling movement in the form of a dorsal flexion or a plantar flexion of the prosthetic foot adapter relative to the prosthetic lower leg is prevented;
    a lower part for fixing the prosthetic foot adapter to the prosthetic foot such that a swiveling movement in the form of a dorsal flexion or a plantar flexion of the prosthetic foot adapter relative to the prosthetic foot is prevented; and a resistance element;

wherein the upper part can be swiveled on the lower part about a swivel axis against a resistance exerted by the resistance element, the swivel axis extending from the heel area to the forefoot area, and the restoring element comprises a torsion bar.

11. The prosthesis according to claim 10, wherein the torsion bar is arranged inside a hollow shaft, which is connected to the upper part or the lower part such that a swiveling movement in the form of a dorsal flexion or a plantar flexion of the hollow shaft relative to the upper part or the lower part is prevented.

12. The prosthesis according to claim 11, wherein the torsion bar is positively connected to the hollow shaft.

13. The prosthesis according to claim 10, wherein the torsion bar has a circular cross-section.

14. The prosthesis according to claim 10, wherein a swiveling of the upper part relative to the lower part in at least one direction is restricted by at least one end stop, and the prosthetic foot adapter comprises at least one end stop element that dampens a strike.

15. The prosthesis according to claim 14, wherein at least one of the resistance element and the at least one end stop element can be at least one of replaced and adjusted.

* * * * *